(12) United States Patent
Kojima

(10) Patent No.: US 6,708,551 B2
(45) Date of Patent: Mar. 23, 2004

(54) INSULATOR POSITIONING STRUCTURE OF GAS SENSOR

(75) Inventor: Takashi Kojima, Kasugai (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 10/206,045

(22) Filed: Jul. 29, 2002

(65) Prior Publication Data

US 2003/0024300 A1 Feb. 6, 2003

(30) Foreign Application Priority Data

Aug. 1, 2001 (JP) ........................................ 2001-234061

(51) Int. Cl.[7] ........................ G01N 7/00; G01N 27/407
(52) U.S. Cl. ........................................ 73/31.05; 204/424
(58) Field of Search .................... 73/31.05, 31.06; 204/424–429

(56) References Cited

U.S. PATENT DOCUMENTS

| | | | | |
|---|---|---|---|---|
| 4,636,293 A | * | 1/1987 | Bayha et al. | 204/428 |
| 5,886,248 A | * | 3/1999 | Paulus et al. | 73/23.31 |
| 6,039,856 A | * | 3/2000 | Weyl et al. | 204/400 |
| 6,063,249 A | * | 5/2000 | Duce et al. | 204/424 |
| 6,164,120 A | * | 12/2000 | Friese et al. | 73/23.2 |
| 6,258,234 B1 | * | 7/2001 | Watanabe et al. | 204/424 |
| 6,477,887 B1 | * | 11/2002 | Ozawa et al. | 73/31.05 |
| 2001/0022104 A1 | * | 9/2001 | Hibino et al. | 73/31.05 |
| 2001/0023612 A1 | * | 9/2001 | Kojima | 73/31.05 |
| 2001/0025522 A1 | * | 10/2001 | Kojima | 73/31.05 |
| 2001/0045120 A1 | * | 11/2001 | Friese et al. | 73/23.31 |
| 2002/0003088 A1 | * | 1/2002 | Ozawa | 204/424 |
| 2002/0014411 A1 | * | 2/2002 | Shirai | 204/424 |
| 2002/0195339 A1 | * | 12/2002 | Nakamura et al. | 204/428 |

FOREIGN PATENT DOCUMENTS

JP  2001-188060  7/2001

\* cited by examiner

*Primary Examiner*—Michael Cygan
(74) *Attorney, Agent, or Firm*—Nixon & Vanderhye P.C.

(57) ABSTRACT

An improved structure of a gas sensor made up of a sensor element and a first and a second hollow cylindrical porcelain insulators covering the sensor element. The first porcelain insulator is laid on the second porcelain insulator in alignment within a body of the gas sensor. A positioning mechanism is provided which works to establish and keep alignment of the first and second porcelain insulators, thereby avoiding undesirable inclination of the first and second porcelain insulators which may cause damage to the sensor element.

6 Claims, 13 Drawing Sheets

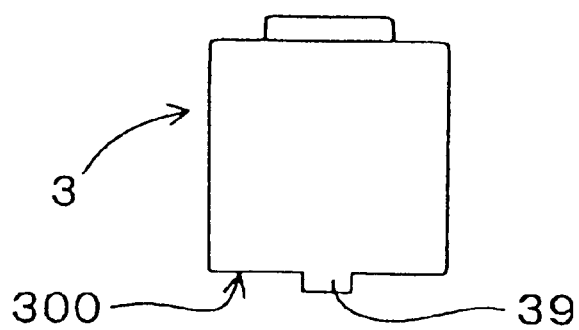
FIG. 8(a)
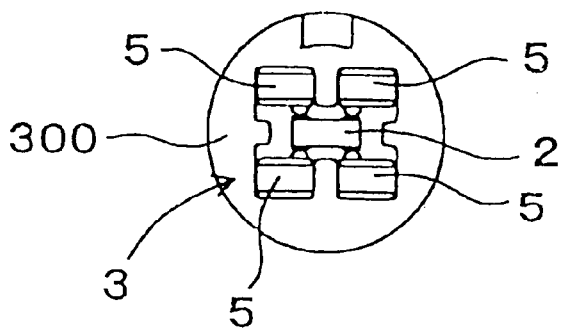
FIG. 8(b)
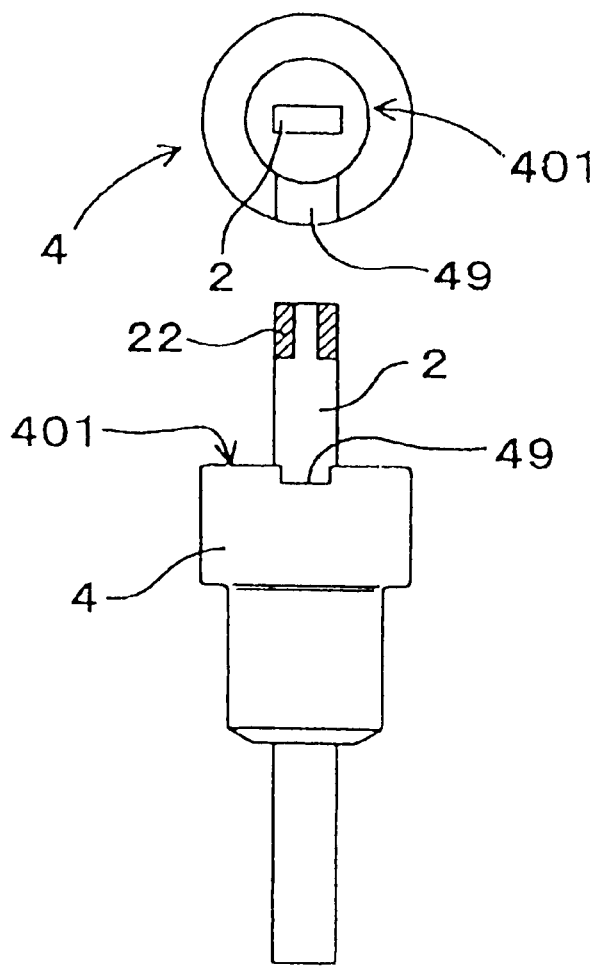
FIG. 8(c)
FIG. 8(d)

PRIOR ART

INSULATOR POSITIONING STRUCTURE OF GAS SENSOR

BACKGROUND OF THE INVENTION

1. Technical Field of the Invention

The present invention relates generally to a gas sensor which may be installed in an exhaust system of an internal combustion engine for air-fuel ratio control, and more particularly to an improved positioning structure of a gas sensor which works to establish a desired positional relation between two porcelain insulators within a body of the gas sensor.

2. Background Art

Gas sensors are known which are installed in an exhaust system of an automotive engine to measure, for example, the concentration of oxygen in exhaust emissions of the engine for air-fuel ratio control.

FIGS. 13(a), 13(b), and 14 show porcelain insulators 93 and 94 which are employed typically in the above type of gas sensor.

The porcelain insulator 94 retains therein a sensor element 2 vertically as viewed in the drawings. The sensor element 2 has a base portion extending outside the porcelain insulator 94. The porcelain insulator 93 is laid on the porcelain insulator 94 in alignment and covers the base portion of the sensor element 2.

The porcelain insulator 93 has formed therein a chamber within which insulating ribs 931 are formed to define contact chambers. Within each contact chamber, a contact spring (not shown) is installed which establishes an electric contact between a lead extending to an external sensor control circuit and each terminal 22 formed on the base portion of the sensor element 2.

The illustrated structure, however, may result in, as shown in FIG. 14, misalignment of longitudinal center lines 930 and 940 of the porcelain insulators 93 and 94 when joined together. This causes the porcelain insulator 93 to be shifted laterally at a contact point B, thereby resulting in a physical hit of one of the ribs 931, as indicated by A, on the sensor element 2, causing damage to the sensor element 2. This problem will be objectionable, especially in a case where the volume of the chamber of the porcelain insulator 93 is decreased in order to decrease the overall size of the gas sensor.

SUMMARY OF THE INVENTION

It is therefore a principal object of the invention to avoid the disadvantages of the prior art.

It is another object of the invention to provide an improved structure of a gas sensor which is designed to assure relative positioning of porcelain insulators without damage to a sensor element.

According to one aspect of the invention, there is provided a gas sensor which may be installed in an exhaust system of an automotive internal combustion engine to measure the concentration of oxygen for use in air-fuel ratio control of the engine. The gas sensor comprises: (a) a hollow cylindrical housing; (b) a sensor element having a length which includes a sensing portion and a base portion, the sensor element being disposed within the housing with the sensing portion projecting from a front end of the housing and the base portion projecting from a rear end of the housing; (c) a front cover installed on the front end of the housing to cover the sensing portion of the sensor element; (d) a base cover installed on the rear end of the housing; (e) a first hollow cylindrical porcelain insulator disposed within the base cover into which the base portion of the sensor element extends; (f) a second hollow cylindrical porcelain insulator disposed in the housing, the second hollow cylindrical porcelain insulator being abutted to the first hollow cylindrical porcelain insulator in alignment with each other; (g) contact members disposed within a chamber defined inside the first hollow cylindrical porcelain insulator, each of the contact members working to establish an electric contact between an electric terminal of the sensor element and a lead extending outside the gas sensor; and (h) a positioning mechanism working to establish a given positional relation between the first and second hollow cylindrical porcelain insulators. This achieves alignment of the first and second porcelain insulators, thus avoiding undesirable inclination of the first and second porcelain insulators relative to each other which may cause damage to the sensor element.

In the preferred mode of the invention, the first hollow cylindrical porcelain insulator is in contact of a front end thereof with a rear end of the second hollow cylindrical porcelain insulator. The positioning mechanism is made up of a protrusion formed on one of the front end of the first hollow cylindrical porcelain insulator and the rear end of the second hollow cylindrical porcelain insulator and a recess formed in the other of the front end of the first hollow cylindrical porcelain insulator and the rear end of the second hollow cylindrical porcelain insulator. The protrusion is engaged in the recess.

The contact members exert elastic pressures on the sensor element to restrain the sensor element from moving in first opposite directions. The positioning mechanism is so designed as to hold the first and second hollow cylindrical porcelain insulators from moving in second opposite directions perpendicular to the first opposite directions.

The positioning mechanism may alternatively be made up of mating portions of the first and second hollow cylindrical porcelain insulators and a mating member. The mating member is engaged in the mating portions of the first and second hollow cylindrical porcelain insulators.

The positioning mechanism may alternatively be made up of markers provided on the first and second hollow cylindrical porcelain insulators.

According to another aspect of the invention, there is provided a gas sensor which comprises: (a) a hollow cylindrical housing; (b) a sensor element having a length which includes a sensing portion and a base portion, the sensor element being disposed within the housing with the sensing portion projecting from a front end of the housing and the base portion projecting from a rear end of the housing; (c) a front cover installed on the front end of the housing to cover the sensing portion of the sensor element; (d) a base cover installed on the rear end of the housing; (e) a first hollow cylindrical porcelain insulator disposed within the base cover into which the base portion of the sensor element extends; (f) a second hollow cylindrical porcelain insulator disposed in the housing, the second hollow cylindrical porcelain insulator being abutted to the first hollow cylindrical porcelain insulator in alignment with each other; (g) contact members disposed within a chamber defined inside the first hollow cylindrical porcelain insulator, each of the contact members working to establish an electric contact between an electric terminal of the sensor element and a lead extending outside the gas sensor, the contact members exerting elastic pressures on the sensor element to restrain the sensor element from moving in first opposite directions;

and (h) a restraining mechanism working to restrain relative motion of the first and second hollow cylindrical porcelain insulators in second opposite directions traversing the first opposite directions while allowing the first and second hollow cylindrical porcelain insulators to be moved in opposite directions substantially identical with the first opposite directions.

In the preferred mode of the invention, the first hollow cylindrical porcelain insulator is in contact of a front end thereof with a rear end of the second hollow cylindrical porcelain insulator. The restraining mechanism is made up of a protrusion formed on one of the front end of the first hollow cylindrical porcelain insulator and the rear end of the second hollow cylindrical porcelain insulator and a recess formed in the other of the front end of the first hollow cylindrical porcelain insulator and the rear end of the second hollow cylindrical porcelain insulator. The protrusion is engaged in the recess.

The restraining mechanism may alternatively be made up of mating portions of the first and second hollow cylindrical porcelain insulators and a mating member. The mating member is engaged in the mating portions of the first and second hollow cylindrical porcelain insulators.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 8(a) is a side view which shows a first porcelain insulator according to the third embodiment of the invention;

FIG. 8(b) is a plan view of FIG. 8(a);

FIG. 8(c) is a plan view which shows a second porcelain insulator according to the third embodiment of the invention which is to be joined to the first porcelain insulator of FIGS. 8(a) and 8(b);

FIG. 8(d) is a side view which shows the second porcelain insulator of FIG. 8(c) within which a sensor element is disposed;

DESCRIPTION OF THE PREFERRED EMBODIMENTS

Figure 1:
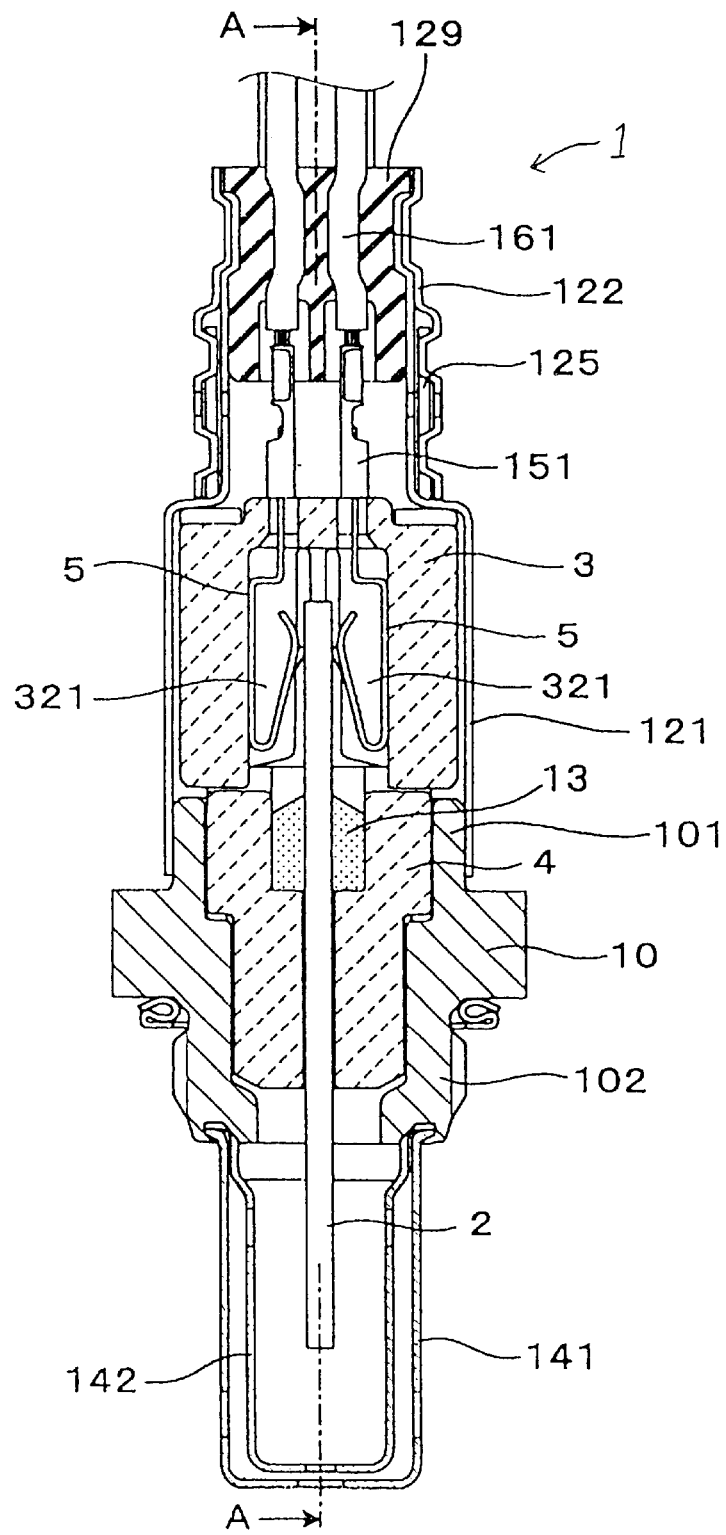
FIG. 1 is a longitudinal sectional view which shows a gas sensor according to the first embodiment of the invention.
Figure 2:
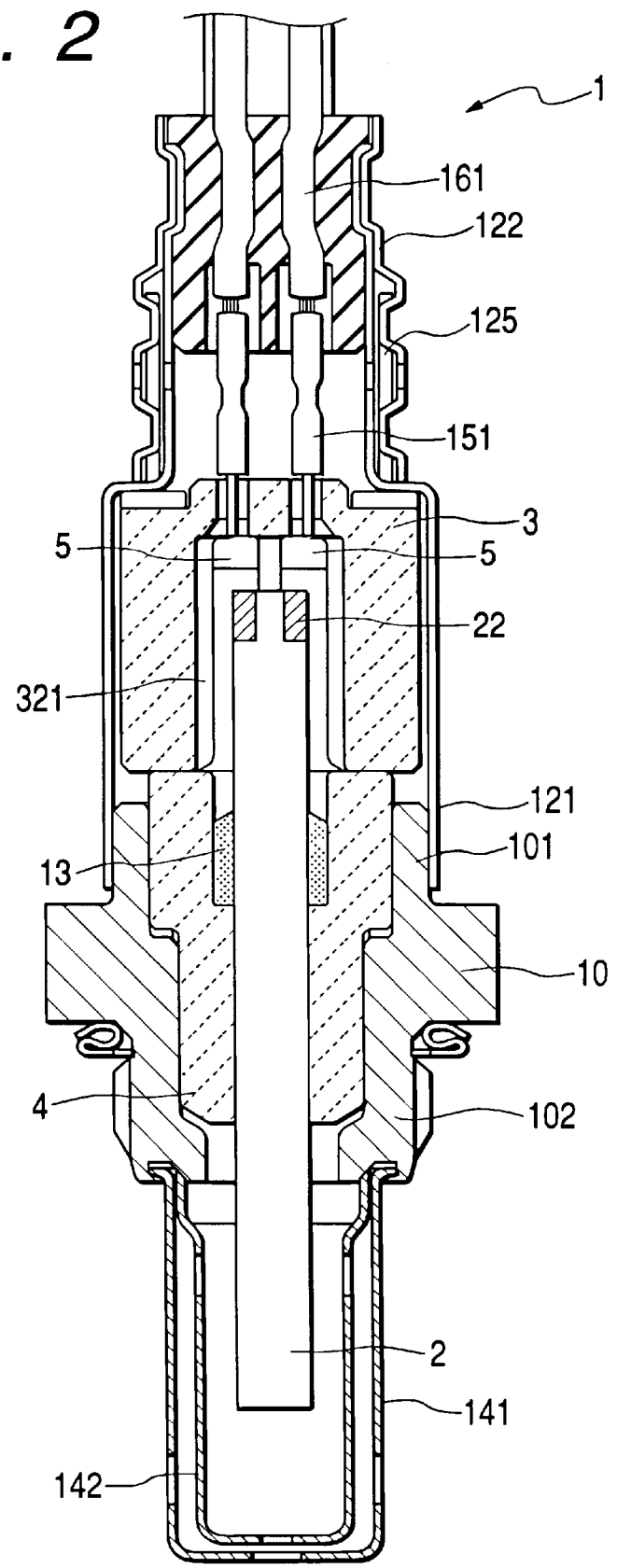
FIG. 2 is a longitudinal sectional view taken along the line A—A in FIG. 1.

Referring to the drawings, wherein like reference numbers refer to like parts in several views, particularly to FIGS. 1 and 2, there is shown a gas sensor 1 according to the first embodiment of the invention which may be employed in a burning control system for automotive vehicles to measure concentrations of components such as NOx, CO, HC, and $O_2$ contained in exhaust gasses of the engine.

The gas sensor 1 generally includes a sensor element 2, a first hollow cylindrical porcelain insulator 3, a second hollow cylindrical porcelain insulator 4, a hollow cylindrical housing 10, an air cover 121, and a protective cover assembly made up of outer and inner covers 141 and 142. The sensor element 2 is made of a laminated plate which consists essentially of a solid-electrolyte layer(s), an insulating layer (s), and a heater. The insulating layer(s) may alternatively be omitted. The sensor element 2 has a given length made up of a sensing portion and a base portion. For example, U.S. Pat. No. 5,573,650 issued on Nov. 12, 1966 to Fukaya et al. teaches a typical laminated sensor element, disclosure of which is incorporated herein by reference. The second porcelain insulator 4 is fitted within the housing 10 and holds therein the sensor element 2. The first porcelain insulator 3 is mounted on the second porcelain insulator 4 in alignment with each other and surrounds the base portion of the sensor element 2. The air cover 121 is installed at an end 101 thereof on the housing 10 to cover the first porcelain insulator 3. The protective cover assembly has a double-walled structure made up of the outer and inner covers 141 and 142 and is installed and staked in an annular groove formed in an end 101 of the housing 10 to cover the sensing portion of the sensor element 2.

Figure 3:
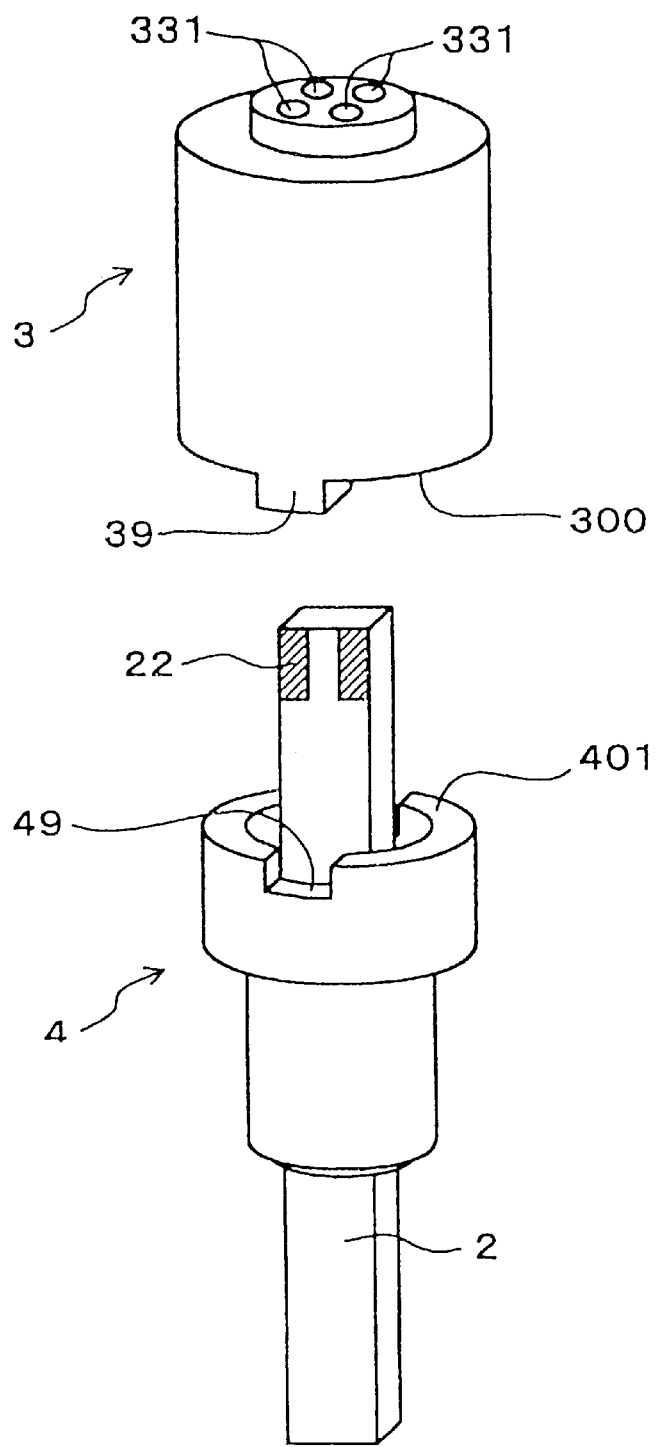
FIG. 3 is a perspective view which show first and second porcelain insulator which are to be aligned to each other when assembled.
Figure 5:
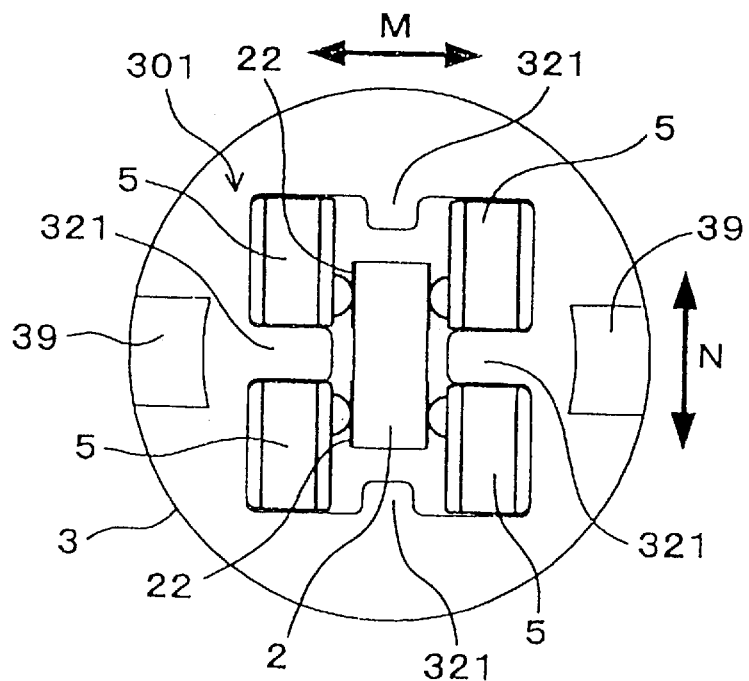
FIG. 5 is a plan view which shows a first porcelain insulator 3, as viewed from a front end surface thereof.
Figure 6:
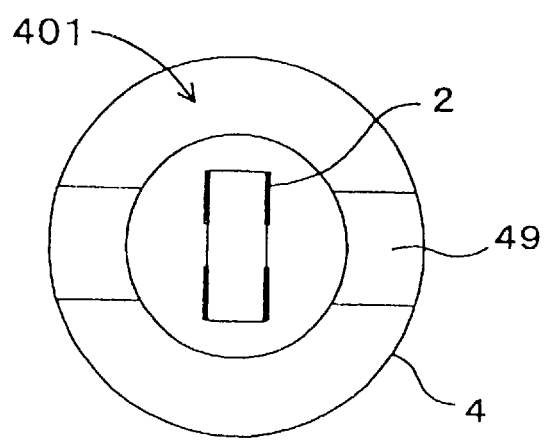
FIG. 6 is a plan view which shows a second porcelain insulator, as viewed from a rear end surface thereof.

C-shaped contact springs 5 are disposed within the first porcelain insulator 3 in contact with terminals 22, as illustrated in FIG. 3, of the sensor element 2 and establish electric connections between the terminals 22 and leads 161 extending to an external sensor control circuit (not shown). The first porcelain insulator 3, as clearly shown in FIG. 3, has formed on a front end surface 300 thereof two protrusions 39 which are engaged in mating recesses 49 formed in a rear end surface 401 of the second porcelain insulator 4, respectively, thereby establishing a desired positional relation therebetween. The protrusions 39 are, as shown in FIG. 5, diametrically opposed to each other, that is, arranged symmetrically about the center of the front end surface 300 of the first porcelain insulator 3. Similarly, the recesses 49 are, as shown in FIG. 6, arranged symmetrically about the center of the rear end surface 401 of the second porcelain insulator 4.

The sensor element 2 is, as described above, retained within the housing 10 and made of a ceramic material. The sensor element 2 has the terminals 22 formed on opposed surfaces thereof. The terminals 22 lead to outer and inner electrodes (not shown) formed on outer and inner surfaces of the sensing portion of the sensor element 2, respectively. The outer electrode is exposed to a measurement gas introduced into a gas chamber defined inside the inner cover 142. The inner electrode is exposed to air introduced as a reference gas into an air chamber defined inside the sensor element 2. The outer and inner electrodes produce a sensor output as a function of the concentration of the measurement gas. The sensor output is transmitted to the external sensor control circuit through the terminals 22, the contact springs 5, and the leads 161. The outer and inner electrodes will also be referred to as a measurement gas electrode and a reference gas electrode below.

Two of the terminals 22 other than those connected to the outer and inner electrodes of the sensor element 2 are joined to a heater which is built in the sensor element 2 and supplied with electric power from the external sensor control circuit to heat the sensor element 2 up to a desired activation temperature.

The air cover 121 is, as clearly shown in FIG. 1, welded to the periphery of the housing 10. The outer cover 122 is provided around the air cover 121 and staked or crimped to retain a water-repellent filter 125 on the periphery of the air cover 121.

The second porcelain insulator 4 is retained within the housing 10 hermetically and holds therein the sensor element 2 through a glass sealing member 13.

An insulating holder 129 made of rubber is disposed inside a small-diameter portion of the air cover 121. An air chamber is defined between the bottom of the insulating holder 129 and a base end (i.e., an upper end, as viewed in FIGS. 1 and 2) of the first porcelain insulator 3. The insulating holder 129 has formed therein four through holes (only two are shown for the brevity of illustration) into which the four leads 161 are inserted, respectively. The holes 141 have defined therein large-diameter bores in which the leads 161 are joined to connectors 151 leasing to the contact springs 5, respectively.

Figure 4A:
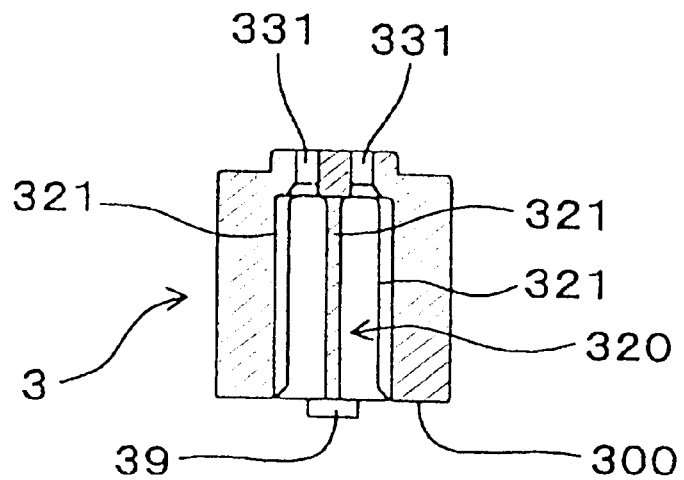
FIG. 4(a) is a sectional view which shows an internal structure of a first porcelain insulator.
Figure 4B:
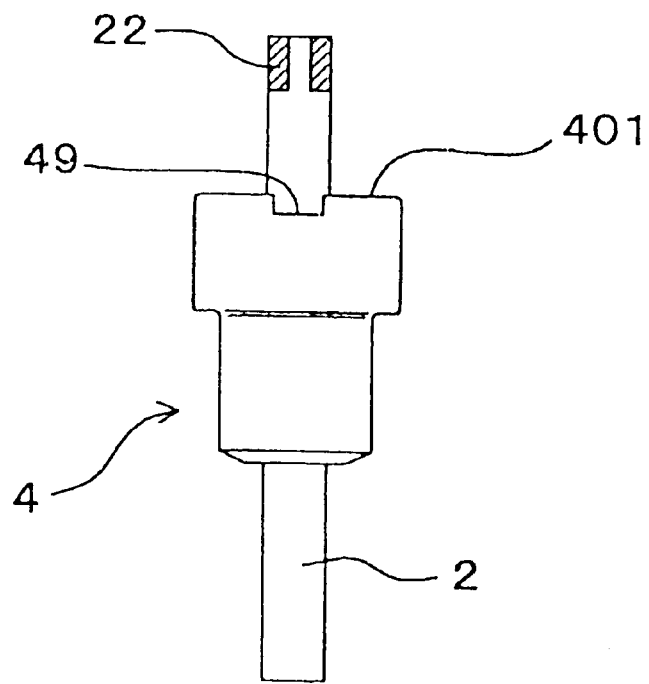
FIG. 4(b) is a side view which shows a second porcelain insulator through which a sensor element is installed.

The first porcelain insulator 3, as can be seen from FIGS. 3 and 4(a), has formed in the base end thereof four holes 331 each having a substantially square cross section through which ends of the contact springs 5 extend. The holes 331 communicate with a sensor element chamber 320 in which the base portion of the sensor element 2 is disposed. Four ribs 321, as clearly shown in FIGS. 4(a) and 5, are formed on an inner wall of the first porcelain insulator 3 to define contact spring chambers which work to fix locations of the contact springs 5 and insulate them from each other.

Each of the contact springs 5, as clearly shown in FIG. 5, has a protrusion which establishes an electric contact with one of the terminals 22 of the sensor element 2. Two of the terminals 22, as described above, work to transmit a sensor output to the external sensor control circuit, while the other terminals 22 work to supply the power to the heater built in the sensor element 2 from the external sensor control circuit.

The contact springs 5 also work to produce elastic pressures in first opposite directions, as indicated by an arrow M in FIG. 5 to hold the base portion of the sensor element 2 tightly at the center of the first porcelain insulator 3. The protrusions 39 are, as described above, formed on the front end surface 300 of the first porcelain insulator 3. A line passing through the protrusions 39 extends parallel to the arrow M. The protrusions 39 are fitted in the recesses 49 of the second porcelain insulator 4 to construct a restraining mechanism which restrains the first and second porcelain insulators 3 and 4 from moving in second opposite directions, as indicated by an arrow N, oriented substantially perpendicular to the first opposite directions. Specifically, the first and second porcelain insulators 3 and 4 are allowed to move in the first opposite directions, thereby absorbing an excess of the elastic pressures of the contact springs 5 acting on the sensor element 2 which may cause damage to the sensor element 2.

Figure 14:
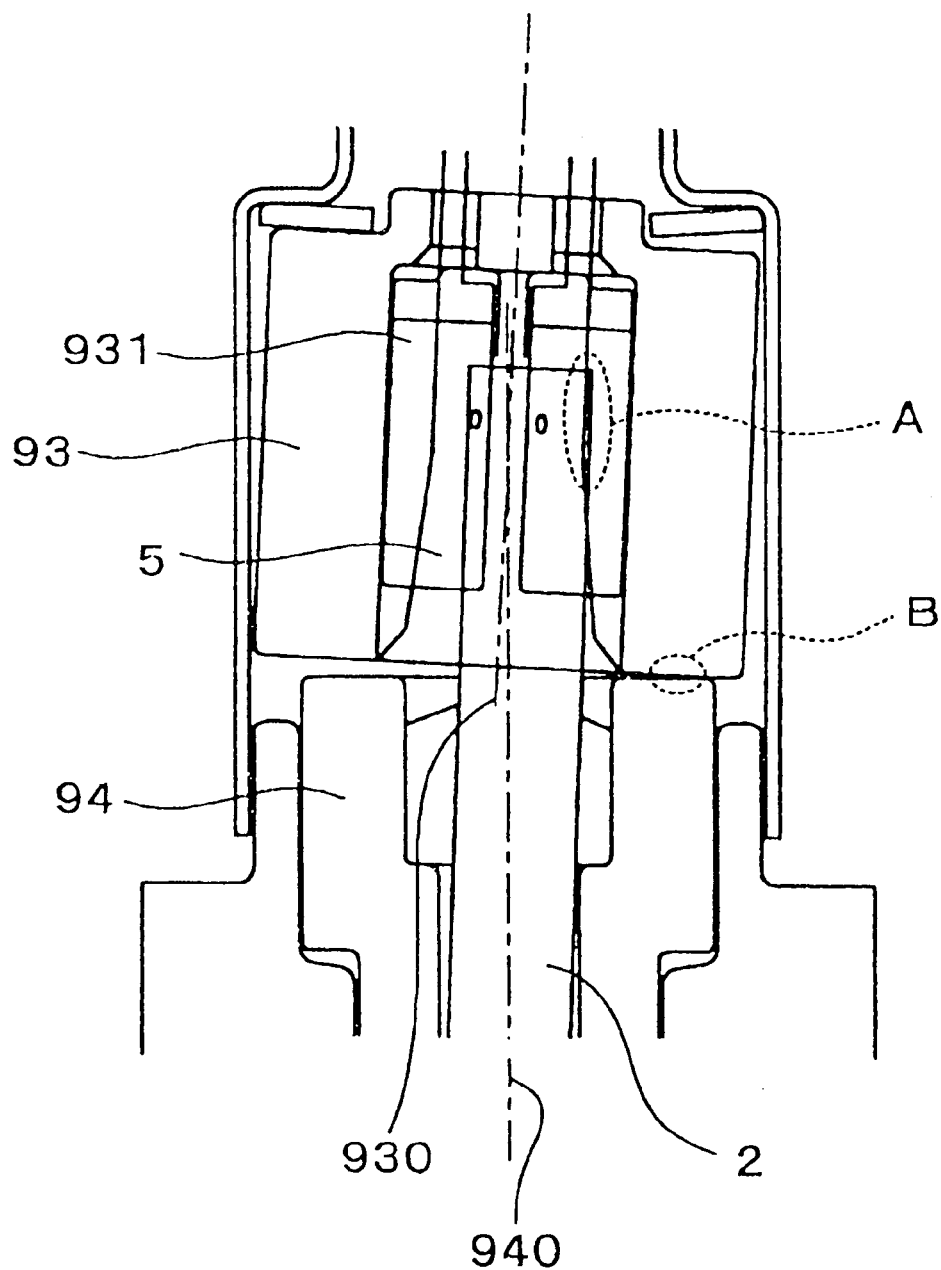
FIG. 14 is a partially sectional view which shows a conventional gas sensor within which the porcelain insulators of FIGS. 13(a) and 13(b) are installed.

The protrusions 39 and the recesses 49 function as an insulator positioning mechanism which works to position the first and second porcelain insulators 3 and 4 in alignment with each other when joined together, thereby holding the sensor element 2 in a desired position within the center of the first porcelain insulator 3 and resulting in ease of dimensional design of the ribs 321 without physical interference with the sensor element 2, thus assuring electric contacts between the contact springs 5 and the terminals 22 of the sensor element 2 under suitable spring pressures without exerting an excessive pressure on the sensor element 2 within the first porcelain insulator 3 which may cause damage to the sensor element 2 in the conventional structure as illustrated in FIG. 14.

Figure 7A:
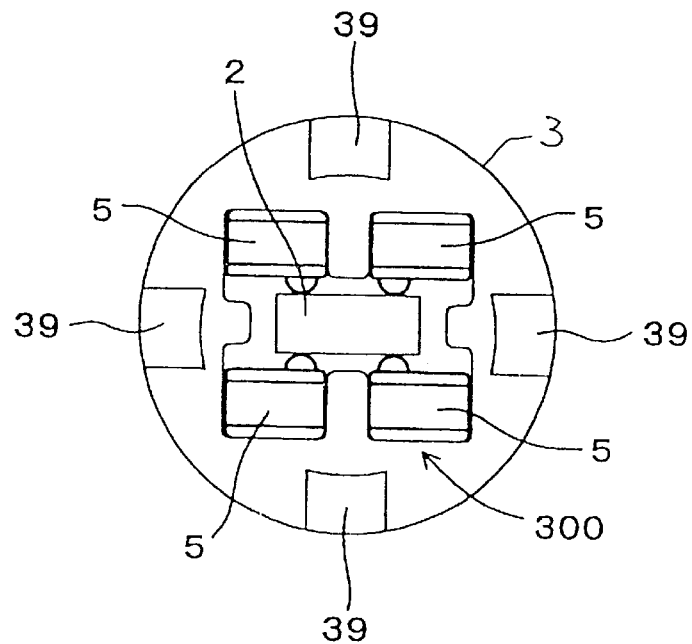
FIG. 7(a) is a plan view which shows a first porcelain insulator 3, as viewed from a front end surface thereof according to the second embodiment of the invention.
Figure 7B:
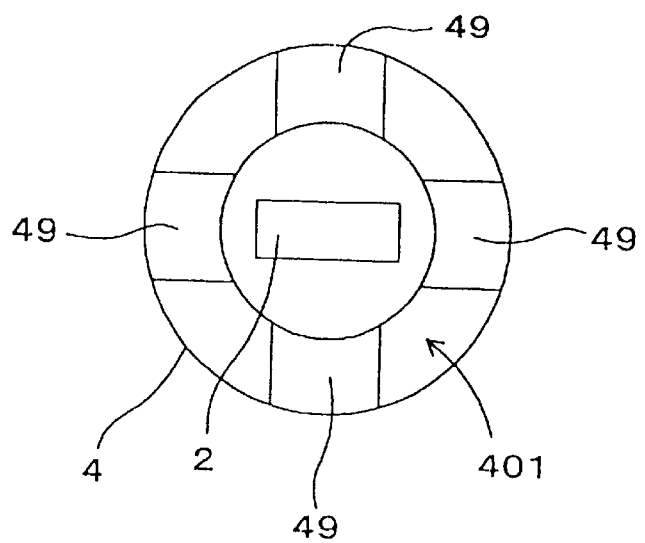
FIG. 7(b) is a plan view which shows a second porcelain insulator, as viewed from a rear end surface thereof according to the second embodiment of the invention.
Figure 9A:
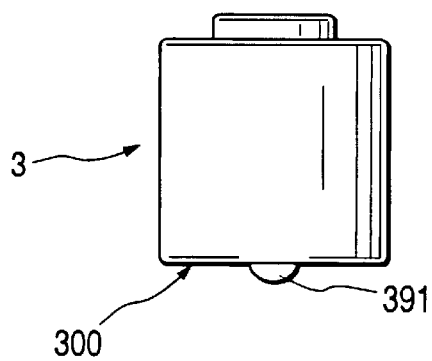
FIG. 9(a) is a side view which shows a first porcelain insulator according to the fourth embodiment of the invention.
Figure 9B:
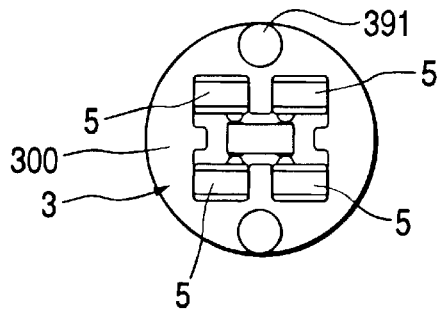
FIG. 9(b) is a plan view of FIG. 9(a)
Figure 9C:
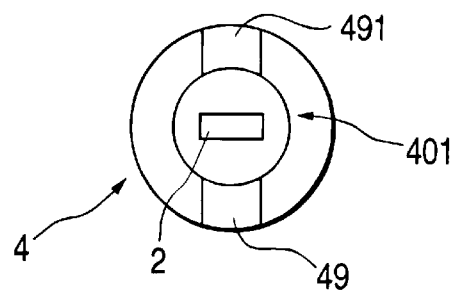
FIG. 9(c) is a plan view which shows a second porcelain insulator according to the fourth embodiment of the invention which is to be joined to the first porcelain insulator of FIGS. 9(a) and 9(b)
Figure 9D:
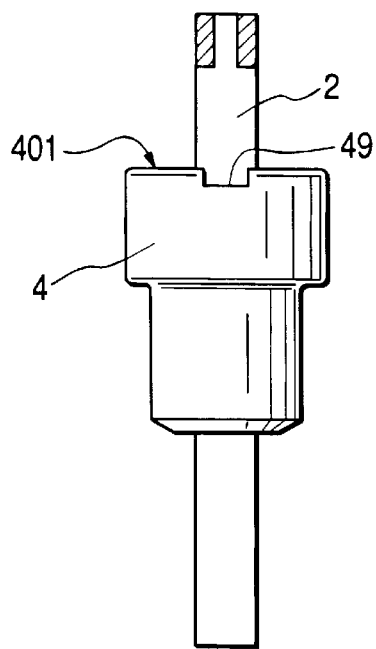
FIG. 9(d) is a side view which shows the second porcelain insulator of FIG. 9(c) within which a sensor element is disposed.
Figure 10A:
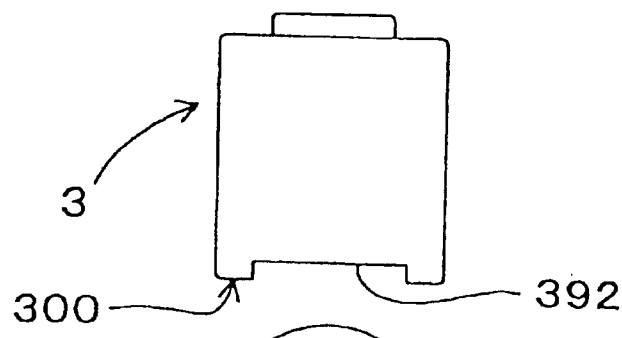
FIG. 10(a) is a side view which shows a first porcelain insulator according to the fifth embodiment of the invention.
Figure 10B:
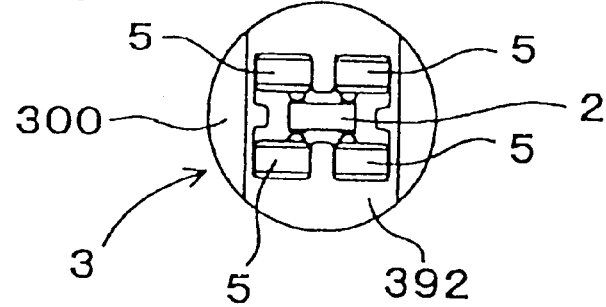
FIG. 10(b) is a plan view of FIG. 10(a)
Figure 10C:
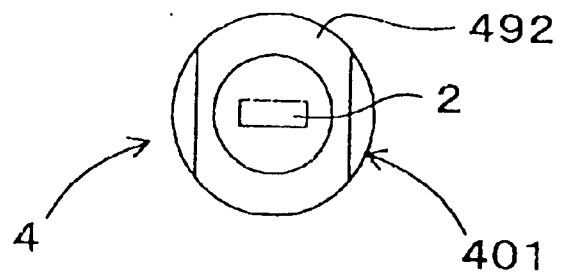
FIG. 10(c) is a plan view which shows a second porcelain insulator according to the fifth embodiment of the invention which is to be joined to the first porcelain insulator of FIGS. 10(a) and 10(b)
Figure 10D:
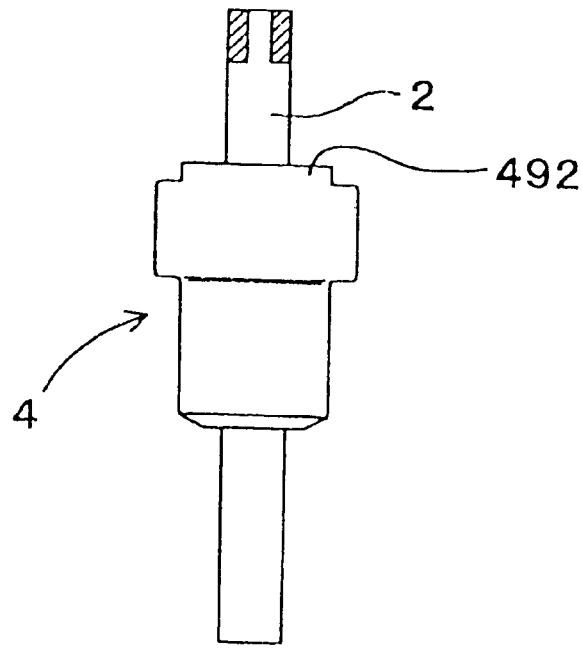
FIG. 10(d) is a side view which shows the second porcelain insulator of FIG. 10(c) within which a sensor element is disposed.

FIGS. 7(a) and 7(b) show the first and second porcelain insulators 3 and 4 according to the second embodiment of the invention.

The first porcelain insulator 3 has four protrusions 39 formed on a circumferential portion of the front end surface 300 at regular angular intervals. The second porcelain insulator 4 has four mating recesses 49 formed in the rear end surface 401 at regular angular intervals. Each of the protrusions 39 is fitted in one of the recesses 49 to joint the first and second porcelain insulators 3 and 4 in a desired position. This holds, like the first embodiment, the sensor element 2 within the center of the first porcelain insulator 3 and results in ease of dimensional design of the ribs 321 without physical interference with the sensor element 2, thus ensuring electric contacts between the contact springs 5 and the terminals 22 of the sensor element 2 under suitable spring pressures without exerting an excess of the pressures on the sensor element 2 within the first porcelain insulator 3.

Other arrangements are identical with those in the first embodiment, and explanation thereof in detail will be omitted here.

FIGS. 8(a) to 8(d) show the first and second porcelain insulators 3 and 4 according to the third embodiment of the invention which is different in structure from the first embodiment only in that a single mating pair of a protrusion 39 and a recess 49 is provided to ensure a desired positional relation between the first and second porcelain insulators 3 and 4 when joined. Other arrangements are identical, and explanation thereof in detail will be omitted here.

The structure of this embodiment, like the above embodiments, serves to avoid undesirable inclination of the first and second porcelain insulators 3 and 4 relative to each other, that is, to establish alignment of the first and second porcelain insulators 3 and 4 when assembled and results in ease of dimensional design of the ribs 321 without physical interference with the sensor element 2, thus ensuring electric contacts between the contact springs 5 and the terminals 22 of the sensor element 2 under suitable spring pressures without exerting an excess of the pressures on the sensor element 2 within the first porcelain insulator 3.

FIGS. 9(a) to 9(d) show the first and second porcelain insulators 3 and 4 according to the fourth embodiment of the invention which is different in structure from the first embodiment only in that each protrusion 391 is hemispherical. Each recess 491 is identical in structure with the one in the first embodiment. Other arrangements are identical with those in the first embodiment, and explanation thereof in detail will be omitted here.

The structure of this embodiment, like the above embodiments, serves to establish the alignment of the first and second porcelain insulators 3 and 4 with each other when assembled, thus ensuring electric contacts between the contact springs 5 and the terminals 22 of the sensor element 2 under suitable spring pressures without exerting an excess of the pressures on the sensor element 2 within the first porcelain insulator 3.

FIGS. 10(a) to 10(d) show the first and second porcelain insulators 3 and 4 according to the fifth embodiment of the invention.

The first porcelain insulator 3 has a single recess 392 formed in a central portion of the front end surface 300. The second porcelain insulator 4 has a mating protrusion 492 formed on a central portion of the rear end surface 401. Other arrangements are identical with those in the first embodiment, and explanation thereof in detail will be omitted here.

The structure of this embodiment, like the above embodiments, serves to establish the alignment of the first and second porcelain insulators 3 and 4 with each other when assembled, thus ensuring electric contacts between the contact springs 5 and the terminals 22 of the sensor element 2 under suitable spring pressures without exerting an excess of the pressures on the sensor element 2 within the first porcelain insulator 3.

Figure 11:
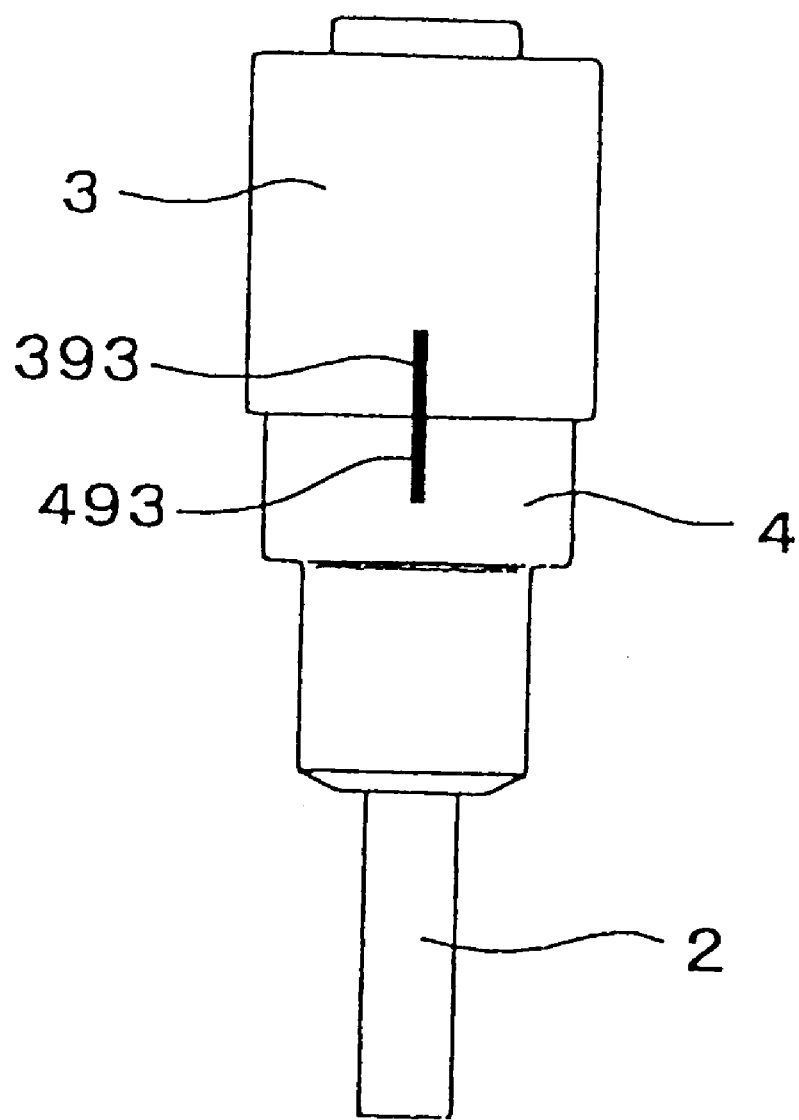
FIG. 11 is a side view which shows first and second porcelain insulators according to the sixth embodiment of the invention.

FIG. 11 shows the first and second porcelain insulators 3 and 4 according to the sixth embodiment of the invention.

The first and second porcelain insulators 3 and 4 have positioning markers 493 and 393 printed on outer walls thereof. Positioning of the first and second porcelain insulators 3 and 4 is accomplished by aligning one of the markers 393 and 493 with the other. Other arrangements are identical with those in the first embodiment, and explanation thereof in detail will be omitted here.

The structure of this embodiment, like the above embodiments, serves to establish the alignment of the first and second porcelain insulator 3 and 4 with each other when assembled, thus ensuring electric contacts between the contact springs 5 and the terminals 22 of the sensor element 2 under suitable spring pressures without exerting an excess of the pressures on the sensor element 2 within the first porcelain insulator 3.

Figure 12A:
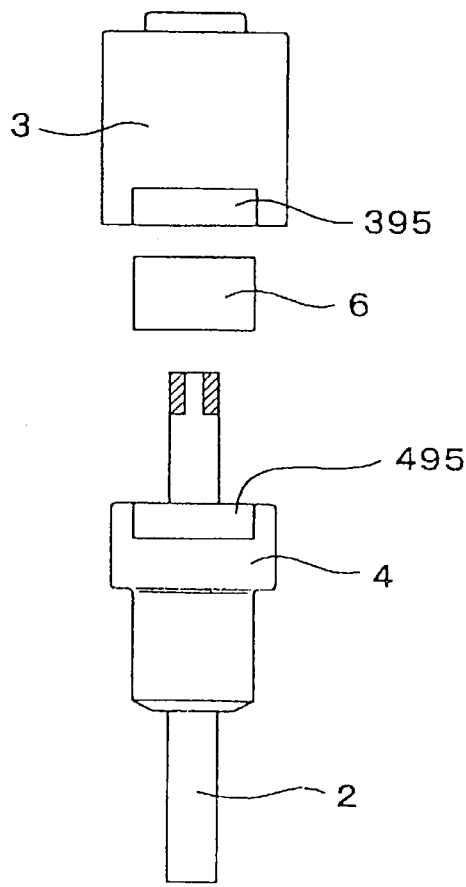
FIG. 12(a) is an exploded view which shows a positioning mechanism for first and second porcelain insulator according to the seventh embodiment of the invention.
Figures 12B, 12C:
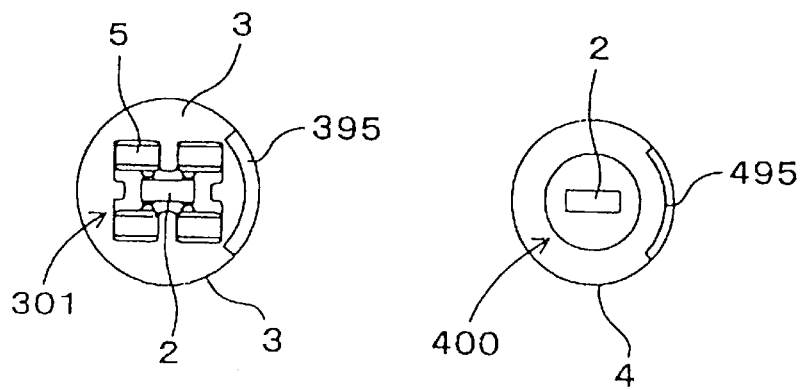
FIG. 12(b) is a plan view which shows the first porcelain insulator of FIG. 12(a)
FIG. 12(c) is a plan view which shows the second porcelain insulator of FIG. 12(a)
Figure 13A:
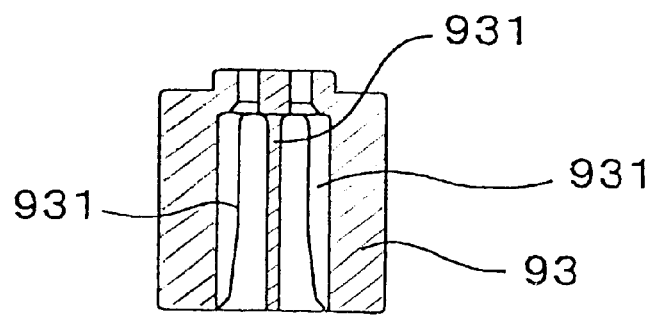
FIG. 13(a) is a sectional view which shows a porcelain insulator used in a conventional gas sensor.
Figure 13B:
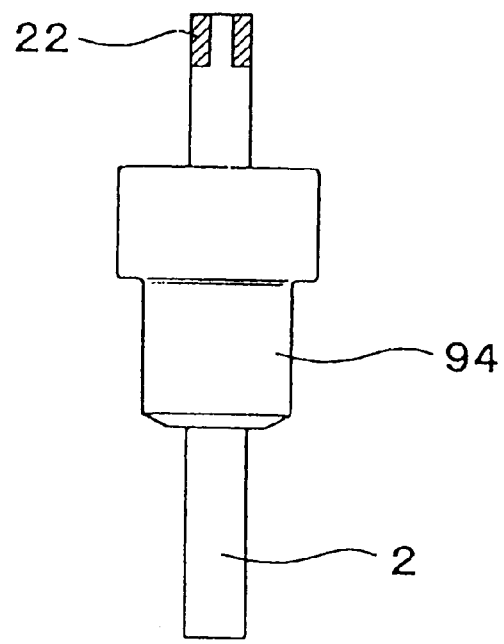
FIG. 13(b) is a side view which shows a porcelain insulator joined to the one of FIG. 13(a)

FIGS. 12(a) to 12(c) show the first and second porcelain insulators 3 and 4 according to the seventh embodiment of the invention.

The first porcelain insulator 3, as clearly shown in FIGS. 12(a) and 12(b), has an arc-shaped recess 395 formed in an outer edge thereof. Similarly, the second porcelain insulator 4, as shown in FIGS. 12(a) and 12(c). has an arc-shaped recess 495 formed in an outer edge thereof. Positioning of the first and second porcelain insulators 3 and 4 is accomplished by fitting an arc-shaped plate 6 both within the recesses 395 and 495. Other arrangements are identical with those in the first embodiment, and explanation thereof in detail will be omitted here.

The structure of this embodiment, like the above embodiments, serves to establish the alignment of the first and second porcelain insulator 3 and 4 with each other when assembled, thus ensuring electric contacts between the contact springs 5 and the terminals 22 of the sensor element 2 under suitable spring pressures without exerting an excess of the pressures on the sensor element 2 within the first porcelain insulator 3.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims. For example, the protrusions formed on the first porcelain insulator 3 in the above embodiments may alternatively be formed on the second porcelain insulator 4, while the mating recesses may be formed in the first porcelain insulator 3.

What is claimed is:

1. A gas sensor comprising:
   a hollow cylindrical housing;
   a sensor element having a length which includes a sensing portion and a base portion, said sensor element being disposed within said housing with the sensing portion projecting from a front end of said housing and the base portion projecting from a rear end of said housing;
   a front cover installed on the front end of said housing to cover the sensing portion of said sensor element;
   a base cover installed on the rear end of said housing;
   a first hollow cylindrical porcelain insulator disposed within said base cover into which the base portion of said sensor element extends;
   a second hollow cylindrical porcelain insulator disposed in said housing, said second hollow cylindrical porcelain insulator being abutted to said first hollow cylindrical porcelain insulator in alignment with each other;
   contact members disposed within a chamber defined inside said first hollow cylindrical porcelain insulator, each of said contact members working to establish an electric contact between an electric terminal of said sensor element and a lead extending outside the gas sensor; and
   a positioning mechanism working to establish a given positional relation between said first and second hollow cylindrical porcelain insulators; and wherein said first hollow cylindrical porcelain insulator is in contact of a front end thereof with a rear end of said second hollow cylindrical porcelain insulator, and wherein said positioning mechanism is made up of a protrusion formed on one of the front end of said first hollow cylindrical porcelain insulator and the rear end of the second hollow cylindrical porcelain insulator and a recess formed in the other of the front end of said first hollow cylindrical porcelain insulator and the rear end of the second hollow cylindrical porcelain insulator, the protrusion being engaged in the recess.

2. A gas sensor comprising:

a hollow cylindrical housing;

a sensor element having a length which includes a sensing portion and a base portion, said sensor element being disposed within said housing with the sensing portion projecting from a front end of said housing and the base portion projecting from a rear end of said housing;

a front cover installed on the front end of said housing to cover the sensing portion of said sensor element;

a base cover installed on the rear end of said housing;

a first hollow cylindrical porcelain insulator disposed within said base cover into which the base portion of said sensor element extends;

a second hollow cylindrical porcelain insulator disposed in said housing, said second hollow cylindrical porcelain insulator being abutted to said first hollow cylindrical porcelain insulator in alignment with each other;

contact members disposed within a chamber defined inside said first hollow cylindrical porcelain insulator, each of said contact members working to establish an electric contact between an electric terminal of said sensor element and a lead extending outside the gas sensor; and a positioning mechanism working to establish a given positional relation between said first and second hollow cylindrical porcelain insulators; and wherein said contact members exert elastic pressures on said sensor element to restrain said sensor element from moving in first opposite directions, and wherein said positioning mechanism is so designed as to hold said first and second hollow cylindrical porcelain insulators from moving in second opposite directions perpendicular to the first opposite directions.

3. A gas sensor comprising:

a hollow cylindrical housing;

a sensor element having a length which includes a sensing portion and a base portion, said sensor element being disposed within said housing with the sensing portion projecting from a front end of said housing and the base portion projecting from a rear end of said housing;

a front cover installed on the front end of said housing to cover the sensing portion of said sensor element;

a base cover installed on the rear end of said housing;

a first hollow cylindrical porcelain insulator disposed within said base cover into which the base portion of said sensor element extends;

a second hollow cylindrical porcelain insulator disposed in said housing, said second hollow cylindrical porcelain insulator being abutted to said first hollow cylindrical porcelain insulator in alignment with each other;

contact members disposed within a chamber defined inside said first hollow cylindrical porcelain insulator, each of said contact members working to establish an electric contact between an electric terminal of said sensor element and a lead extending outside the gas sensor; and a positioning mechanism working to establish a given positional relation between said first and second hollow cylindrical porcelain insulators; and wherein said positioning mechanism is made up of mating portions of said first and second hollow cylindrical porcelain insulators and a mating member, the mating member being engaged in the mating portions of said first and second hollow cylindrical porcelain insulators.

4. A gas sensor comprising:

a hollow cylindrical housing;

a sensor element having a length which includes a sensing portion and a base portion, said sensor element being disposed within said housing with the sensing portion projecting from a front end of said housing and the base portion projecting from a rear end of said housing;

a front cover installed on the front end of said housing to cover the sensing portion of said sensor element;

a base cover installed on the rear end of said housing;

a first hollow cylindrical porcelain insulator disposed within said base cover into which the base portion of said sensor element extends;

a second hollow cylindrical porcelain insulator disposed in said housing, said second hollow cylindrical porcelain insulator being abutted to said first hollow cylindrical porcelain insulator in alignment with each other;

contact members disposed within a chamber defined inside said first hollow cylindrical porcelain insulator, each of said contact members working to establish an electric contact between an electric terminal of said sensor element and a lead extending outside the gas sensor; and a positioning mechanism working to establish a given positional relation between said first and second hollow cylindrical porcelain insulators; and wherein said positioning mechanism is made up of markers provided on said first and second hollow cylindrical porcelain insulators.

5. A gas sensor comprising:

a hollow cylindrical housing;

a sensor element having a length which includes a sensing portion and a base portion, said sensor element being disposed within said housing with the sensing portion projecting from a front end of said housing and the base portion projecting from a rear end of said housing;

a front cover installed on the front end of said housing to cover the sensing portion of sensor element;

a base cover installed on the rear end of said housing;

a first hollow cylindrical porcelain insulator disposed within said base cover into which the base portion of said sensor element extends;

a second hollow cylindrical porcelain insulator disposed in said housing, said second hollow cylindrical porcelain insulator being abutted to said first hollow cylindrical porcelain insulator in alignment with each other;

contact members disposed within a chamber defined inside said first hollow cylindrical porcelain insulator, each of said contact members working to establish an electric contact between an electric terminal of said sensor element and a lead extending outside the gas sensor, said contact members exerting elastic pressures on said sensor element to restrain said sensor element from moving in first opposite directions; and a restraining mechanism working to restrain relative motion of said first and second hollow cylindrical porcelain insulators in second opposite directions traversing the first opposite directions while allowing said first and second hollow cylindrical porcelain insulators to be moved in opposite directions substantially identical with the first opposite directions, wherein said first hollow cylindrical porcelain insulator is in contact of a front end thereof with a rear end of said second hollow cylindrical porcelain insulator, and wherein said restraining mechanism is made up of a protrusion formed on one of the front end of said first hollow cylindrical porcelain insulator and the rear end of the second hollow cylindrical porcelain insulator and a recess formed in the other of the front end of said first hollow cylindrical porcelain insulator and the rear end of the second hollow cylindrical porcelain insulator, the protrusion being engaged in the recess.

6. A gas sensor a hollow cylindrical housing;

a sensor element having a length which includes a sensing portion and a base portion, said sensor element being disposed within said housing with the sensing portion projecting from a front end of said housing and the base portion projecting from a rear end of said housing;

a front cover installed on the front end of said housing to cover the sensing portion of said sensor element;

a base cover installed on the rear end of said housing;

a first hollow cylindrical porcelain insulator disposed within said base cover into which the base portion of said sensor element extends;

a second hollow cylindrical porcelain insulator disposed in said housing, said second hollow cylindrical porcelain insulator being abutted to said first hollow cylindrical porcelain insulator in alignment with each other;

contact members disposed within a chamber defined inside said first hollow cylindrical porcelain insulator, each of said contact members working to establish an electric contact between an electric terminal of said sensor element and a lead extending outside the gas sensor, said contact members exerting elastic pressures on said sensor element to restrain said sensor element from moving in first opposite directions; and a restraining mechanism working to restrain relative motion of said first and second hollow cylindrical porcelain insulators in second opposite directions traversing the first opposite directions while allowing said first and second hollow cylindrical porcelain insulators to be moved in opposite directions substantially identical with the first opposite directions, wherein said restraining mechanism is made up of mating portions of said first and second hollow cylindrical porcelain insulators and a mating member, the mating member being engaged in the mating portions of said first and second hollow cylindrical porcelain insulators.

* * * * *